(12) United States Patent
Michalopoulos et al.

(10) Patent No.: US 6,737,270 B1
(45) Date of Patent: May 18, 2004

(54) LONG-TERM THREE DIMENSIONAL TISSUE CULTURE SYSTEM

(75) Inventors: George Michalopoulos, Bethel, PA (US); William C. Bowen, White Oak, PA (US)

(73) Assignee: University of Pittsburgh of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 09/455,952

(22) Filed: Dec. 7, 1999

(51) Int. Cl.$^7$ .............................. C12N 5/06; C12N 5/08; C12N 11/02; C12N 11/08
(52) U.S. Cl. ..................... 435/373; 424/93.7; 435/177; 435/180; 435/395; 435/402; 435/405
(58) Field of Search ................................ 435/177, 180, 435/395, 373, 402, 405; 424/93.7

(56) References Cited

U.S. PATENT DOCUMENTS

| | | | |
|---|---|---|---|
| 4,853,324 A | 8/1989 | Viles et al. ..................... 435/2 |
| 5,043,260 A | 8/1991 | Jauregui et al. ................ 435/1 |
| 5,270,192 A | 12/1993 | Li et al. ...................... 435/174 |
| 5,298,615 A | * 3/1994 | Matsui et al. .................. 536/56 |
| 5,559,022 A | 9/1996 | Naughton et al. .......... 435/370 |
| 5,624,840 A | 4/1997 | Naughton et al. .......... 435/395 |
| 5,759,830 A | * 6/1998 | Vacanti et al. ............... 435/180 |
| 5,800,537 A | 9/1998 | Bell ............................. 623/11 |
| 5,855,619 A | 1/1999 | Caplan et al. ................. 623/11 |
| 5,885,829 A | 3/1999 | Mooney et al. ............. 435/325 |
| 5,891,455 A | 4/1999 | Sittinger et al. ............ 424/426 |
| 5,910,431 A | 6/1999 | Ni et al. ..................... 435/69.5 |
| 5,910,582 A | 6/1999 | Elliot et al. ................. 534/23.5 |
| 5,942,496 A | 8/1999 | Bonadio et al. .............. 514/44 |

OTHER PUBLICATIONS

Michalopoulos, et al., 1999, "Morphogenetic events in mixed cultures of rat hepatocytes and nonparenchymal cells maintained in biological matrices in the presence of hepatocyte growth factor and epidermal growth factor", *Hepatology* 29:90–100.

Mitaka et al., 1999, "Reconstruction of Hepatic Organoid by Rat Small Hepatocytes and Hepatic Nonparenchymal Cells", *Hepatology* 29:111–125.

Cable, 1997, "Exposure of Primary Rat Hepatocytes in Long–Term DMSO Culture to Selected Transition Metals Induces Hepatocyte Proliferation and Formation of Duct–Like Structures", *Hepatology* 26:1444–1445.

Kay et al., 1997, "Liver regeneration prospects for therapy based on new technologies", *Molecular Medicine Today* 3:108–115.

Block et al., 1996, "Population Expansion, Clonal Growth, and Specific Differentiation Patterns in Primary Cultures of Hepatocytes Induced by HGF/SF/ EGF and TGFα in a Chemically Defined (HGM) Medium", *J. Cell Biol.* 132:1133–1149.

Tateno et al.,1996, "Long–Term Cultivation of Adult Rat Hepatocytes That Undergo Multiple Cell Divisions and Express Normal Parenchymal Phenotypes", *Am. J. Pathol.* 148:383–392.

Fausto et al., 1995, "Role of growth factors and cytokines in hepatic regeneration", *FASEB J.* 9:1527–1536.

Martinez–Hernandez et al., 1995, "The extracellular matrix in hepatic regeneration", *FASEB J.* 9:1401–1409.

Mikata et al., 1995, "Growth and Maturation of Small Hepatocytes Isolated from Adult Rat Liver", *Biochem. Biophys. Res. Commun.* 214:310–317.

Jukkola et al., 1993, "Procollagen synthesis and extracellular matrix deposition in MG–63 osteosarcoma cells", *J. Bone Mineral Research* 8:651–657.

Mikata et al., 1993, "Effects of Mitogens and Co–Mitogens on the Formation of Small–Cell Colonies in Primary Cultures of Rat Hepatocytes", *J. Cell Physiol.* 157:461–468.

Mikata et al., 1993, "Effect of Age on the Formation of Small–Cell Colonies in Cultures of Primary Rat Hepatocytes", *Cancer Res.* 53:3145–3148.

Mikata et al.,1992, "Small Cell Colonies Appear in the Primary Culture of Adult Rat Hepatocytes in the Presence of Nicotinamide and Epidermal Growth Factor", *Hepatology* 16:440–447.

Takezawa et al., 1992, "Morphological and Immuno–Cytochemical Characterization of a Heterospheroid Composed of Fibroblasts and Hepatocytes", *J. Cell Sci.* 101:495–501.

Kost et al., 1991, "Effect of 2% Dimethyl Sulfoxide on the Mitogenic Properties of Epidermal Growth Factor and Hepatocyte Growth Factor in Primary Hepatocyte Culture", *J. Cell Physiol.* 147:274–289.

(List continued on next page.)

*Primary Examiner*—David M. Naff
(74) *Attorney, Agent, or Firm*—Foley Hoag LLP

(57) ABSTRACT

A method is provided for long term culture of proliferating hepatocytes that retain hepatic function to produce a hepatic cell culture. Hepatocytes and nonparenchymal cells are co-cultured ex vivo on a matrix coated with a molecule that promotes cell adhesion, proliferation or survival, in the presence of growth factors, resulting in a long-term culture of proliferating hepatocytes that retain hepatic function. The co-culturing method results in the formation of matrix/hepatic cell clusters that may be mixed with a second structured or scaffold matrix that provides a three-dimensional structural support to form structures analogous to liver tissue counterparts. The method can be used to form bio-articial livers through which a subjects blood is perfused. In an embodiment, the hepatocytes and nonparenchymal cells are derived from disaggregated liver tissue and are co-cultured in the presence of epidermal growth factor or heptocyte growth factor and beads coated with extracellular matrix protein, Alternatively, the hepatic cell culture may be implanted into the body of a recipient host having a hepatic disorder. Such hepatic disorders, include, for example, cirrhosis of the liver, induced hepatitis, chronic hepatitis, primary sclerosing cholangitis and alpha$_1$ antitrypsin deficiency.

6 Claims, 14 Drawing Sheets

OTHER PUBLICATIONS

Figure 1A:
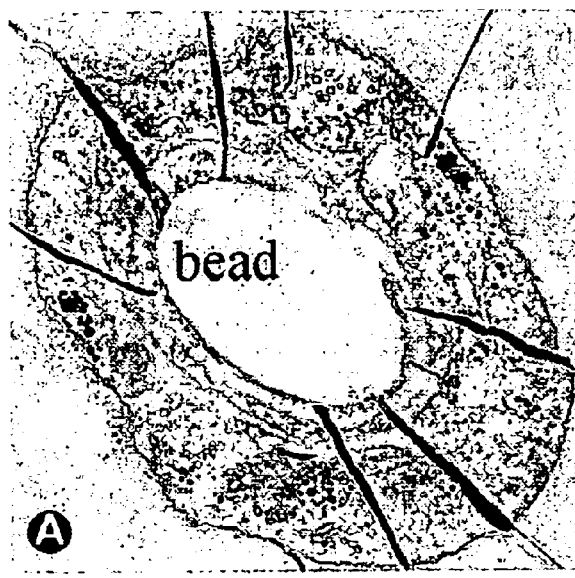

Mikata et al., 1991, "Multiple Cell Cycles Occur in Rat Hepatocytes Cultured in the Presence of Nicotinamide and Epidermal Growth Factor", *Hepatology 13*:21–30.

Ausebel et al., 1989, *Current Protocols in Molecular Biology*, Greene Publishing Associates & Wiley Interscience, New York.

Sambrook, et al., 1989, *Molecular Cloning: A Laboratory Manual*, Second Edition, Cold Spring Harbor Laboratory Press, New York.

Senoo et al.,1989, "Co–Culture of Fibroblasts and Hepatic Parenchymal Cells Induces Metabolic Changes and Formation of a Three–Dimensional Structure", *Cell Biol. Internat. Reports 13*:197–206.

Freshney,1987, *Culture of Animal Cells, A Manual of Basic Technique*, 2d Ed., A.R. Liss, Inc., New York, Ch.9, pp. 107–126.

Demetriou et al., 1986, "New Method of Hepatocyte Transplantation and Extracorporeal Liver Support", *Ann. Surg. 9*:259–271.

Landry et al., 1985, "Spheroidal Aggregrate Culture of Rat Liver Cells: Histotypic Reorganization, Biomatrix Deposition, and Maintenance of Functional Activities",*J. Cell Biol. 101*:914–923.

Hagger et al., 1983, "Neonatal Hepatocyte Culture on Artificial Capillaries; A model for Drug Metabolism and the Artificial Liver", *ASAIO J. 6*:26–35.

Seglen et al., 1976, "Preparation of isolated rat liver cells", *Methods in Cell Biology 13*:29–83.

* cited by examiner

LONG-TERM THREE DIMENSIONAL TISSUE CULTURE SYSTEM

1. INTRODUCTION

The present invention relates to a novel tissue culture system that provides for the long term culture of proliferating hepatocytes that retain hepatic function. Disclosed are methods and compositions for ex vivo culturing of hepatocytes and nonparenchymal cells on a matrix coated with a molecule that promotes cell adhesion, proliferation or survival, in the presence of growth factors, resulting in a long-term culture of proliferating hepatocytes that retain hepatic function. The co-culturing method results in the formation of matrix/hepatic cell clusters that may be mixed with a second structured or scaffold matrix that provides a three-dimensional structural support to form structures analogous to liver tissue counterparts. The hepatic cell culture system can be used to form bio-artificial livers through which a subjects blood is perfused. Alternatively, the novel hepatic cell culture system may be implanted into the body of a recipient host having a hepatic disorder. Such hepatic disorders, include, for example, cirrhosis of the liver, induced hepatitis, chronic hepatitis, primary sclerosing cholangitis and alpha, antitrypsin deficiency.

The present invention is based on the discovery that mixed cultures of proliferating hepatocytes and nonparenchymal cells, grown on a collagen-coated matrix in medium containing hepatocyte growth factor (HGF) and epidermal growth factor (EGF), maintain their capacity to proliferate while retaining hepatic functions.

2. BACKGROUND OF INVENTION

One of the major functions of the liver is to break down harmful substances absorbed from the intestine or manufactured elsewhere in the body, followed by their excretion as harmless by-products into the bile or blood. Abnormalities of liver function caused by insult to and/or death or malfunction of the cells in the liver can lead to a variety of different hepatic disorders including cirrhosis of the liver or hepatitis. Treatment of such disorders may include whole liver transplants, although this treatment is limited by organ availability, surgical complications, and immunologically-mediated graft rejection normally associated with liver transplantation.

While hepatocyte transplantation has been considered as an alternative to whole-organ transplantation, major technical barriers such as the inability to transfer donor hepatocytes into the liver of a recipient, in numbers to provide a beneficial result, have limited the usefulness of this approach. One of the major difficulties in constructing artificial liver tissue is that, to function effectively, the artificial liver tissue requires functionally active, differentiated hepatocytes present at high densities. Future success with artificial liver tissue will depend on the development of systems in which hepatocytes attached to matrices and packed at high density can retain long term their full functional capacity.

To generate artificial liver tissue, it will be necessary to provide in vitro cultures of hepatocytes. Unfortunately, one of the problems associated with the culturing of hepatocytes is that gene expression deteriorates rapidly as the hepatocytes proliferate. Likewise, long-term cultures of hepatocytes having stable gene expression can only be maintained in the absence of cell proliferation. Thus, one of the long-standing goals of culturing hepatocytes is the establishment of proliferating cultures with long-term gene expression.

A number of culture techniques have been developed that permit primary hepatocyte cultures to grow and/or express complex patterns of hepatocyte differentiation (Mitaka, et al., 1995, *Biochem Biophys Res Commun* 214: 310–317; Cable, 1997, *Hepatology* 26: 1444–1445; Block, et al., 1996, *J. Cell Biol.* 132: 1133–1149). Conditions have also been established that allow mature hepatocytes to enter into clonal expansion in cell culture (Block, et al., 1996, *J. Cell Biol.* 132: 1133–1149). For example, hepatocytes cultured in chemically defined hepatocyte growth medium (HGM) enter into DNA synthesis in response to polypeptide mitogens, notably epidermal growth factor (EGF), transforming growth factor-$\alpha$ (TGF-$\alpha$), and hepatocyte growth factor (HGF). These mitogens induce multiple rounds of DNA synthesis and expansion of the cell population. The proliferating cells, however, lose most markers of hepatocyte differentiation while they retain expression of hepatocyte associated transcription factors HNF1, HNF4, and HNF3. In addition, proliferation of adult hepatocytes has been observed in serum-free medium supplemented with nicotinarnide and epidermal growth factor (EGF) (Mitaka, T., et al., 1991, *Hepatology* 12: 21–30; Mitaka, T., et al., 1992, *Hepatology* 10:440–447; Mitaka, T., et al., 1993, *J. Cell Physiol,* 147: 461–468; Mitaka, T., et al., *Cancer Res,* 1993, 53: 3145–3148; Block, G. D., et al., 1996, *J. Cell Biol.* 132:1133–1149; Tateno, C., et al., 1996, *Am J. Pathol* 148: 383–392).

Previous studies have indicated that a fundamental parameter that best determines hepatocyte gene expression in culture is the surrounding matrix. Hepatocytes embedded in complex matrices, such as Matrigel or type I collagen gels, maintain stable phenotypic expression, however, at the expense of cell proliferation. Recently, Mitaka, T. et al. (1999, *Hepatology* 29: 111–125) showed that small hepatocytes could differentiate to mature hepatocytes that interact with hepatic nonparenchymal cells and extracellular matrix. The mature hepatocytes reconstructed three-dimensional structures, expressed proteins known to be expressed in highly differentiated hepatocytes and the cells survived for more than 3 months, while maintaining hepatic differentiated functions. In addition, Landry et al. (1985, *J. Cell Biol.* 101:914–923) demonstrated the reconstruction of a three-dimensional cyto-architecture consisting of differentiated hepatocytes, bile duct-like cells and deposited extracellular matrix by the use of spheroidal aggregate culture of hepatic cells isolated from newborn rats. Three-dimensional cell culture systems have also been disordered in which hepatocytes are grown on a pre-established stromal tissue (U.S. Pat. No. 5,624,840). Attempts have also been made to grow a three-dimensional hepatic organoid using a co-culture of hepatocytes and fibroblasts (Senoo, et al., 1989, *Cell Biol. Internat. Reports* 13:197–206; Takezawa, et al., 1992, *J Cell Sci* 101:495–501).

A number of devices which perform the function of the liver and involve blood perfusion have been described (Hagger et al., 1983, *ASAIO J.* 6:26–35; U.S. Pat. No. 5,043,260; U.S. Pat. No, 5,270,192: Demetriou et al., 1986, *Ann. Surg* 9:259–271). However, a number of problems are associated with the use of such devices for treatment of patients suffering from hepatic failure or dysfunction. Perhaps, the most significant problem is the inability to culture hepatocytes that retain hepatic function for prolonged periods of time, although, attempts have been made to circumvent this problem through the use of transformed hepatocytes that are capable of proliferating indefinitely (U.S. Pat. No. 4,853,324).

Development of a stable support system that would maintain hepatic functions and be useful in stabilizing patients in partial or complete hepatic failure has been a long-term scientific goal in the field of hepatology. Similar devices have revolutionized the treatment of patients with kidney failure and have allowed long-term stabilization of a large population of patients. Currently the use of such devices in treatment of liver failure is quite limited and existing devices are based on rapidly assembled hepatocyte support systems which partially sustain the patient over a very limited period of time, i.e, 24 to 48 hours with declining function over more prolonged term use.

3. SUMMARY OF THE INVENTION

The present invention relates to a novel tissue culture system that provides for long term culture of proliferating hepatocytes that retain their capacity to express hepatic function. The invention generally relates to compositions and methods for generating long term cultures of hepatocytes that can be used to produce three-dimensional hepatic cell culture systems. Such hepatic cell culture systems can be used to form bio-artificial livers that function as perfusion devices. Alternatively, the three-dimensional hepatic cell cultures may be implanted into a subject having a liver disorder.

The method of the present invention comprises the co-culturing of hepatocytes and nonparenchymal cells in the presence of growth factors and a matrix material coated with at least one biologically active molecule that promotes cell adhesion, proliferation or survival. The co-culturing method results in the formation of matrix/hepatic cell clusters containing a mixture of replicating hepatocytes and nonparenchymal cells. The method of the present invention may further comprise the mixing of the matrix/hepatic cell clusters in combination with a second structured, or scaffold matrix, that provides a three-dimensional structural support to form structures analogous to liver tissue counterparts.

Compositions of the present invention include populations of matrix/hepatic cell clusters comprising co-cultures of hepatocytes and nonparenchymal cells bound to a matrix coated with at least one biologically active molecule that promotes cell adhesion, proliferation or survival. Further, the invention provides a three-dimensional hepatic cell matrix system comprising a three-dimensional support matrix containing a population of matrix/hepatic cell clusters comprising hepatocytes and nonparenchymal cells bound to a matrix coated with at least one biologically active molecule that promotes cell adhesion, proliferation or survival.

The compositions of the present invention may be used to form bio-artificial livers through which a host's blood is perfused. Alternatively, the three-dimensional hepatic cell matrix system may be transplanted to a recipient host for providing hepatic function in subjects with liver disorders. The three-dimensional matrix system is administered in an effective amount to provide restoration of liver function, thereby alleviating the symptoms associated with liver disorders. The present invention, by enabling methods for generating long-term cultures of hepatocytes, provides a safer alternative to whole liver transplantation in subjects having liver disorders including, but not limited to, cirrhosis of the liver, alcohol induced hepatitis, chronic hepatitis, primary sclerosing cholangitis and alpha,-antitrypsin deficiency.

4. BRIEF DESCRIPTION OF THE DRAWINGS

Figure 1B:
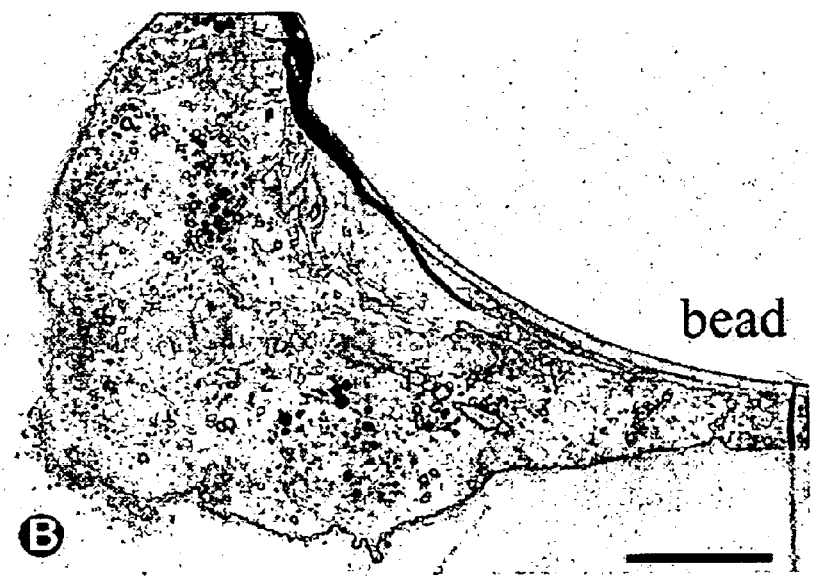

FIGS. 1A–B. Thin sections of cells on beads in roller bottle cultures at day 15 after isolation, stained with toluidine blue.

FIG. 1A. The bead is seen as a hollow space in the center of the cell cluster. Gray material around the bead represents dense type-1 collagen deposition. The collagen surrounds and embeds connective-tissue derived nonparenchymal cells. Cells with hepatocyte morphology surround the connective tissue core.

FIG. 1B. The epithelial cells with hepatocyte morphology form an eccentric growth over a foundation of connective tissue cells. Note the formation of multiple microvilli over the hepatocytes present on the surface.

Figure 2A:
Figure 2B:
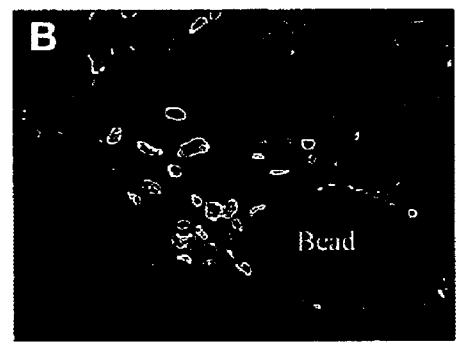
Figure 2C:
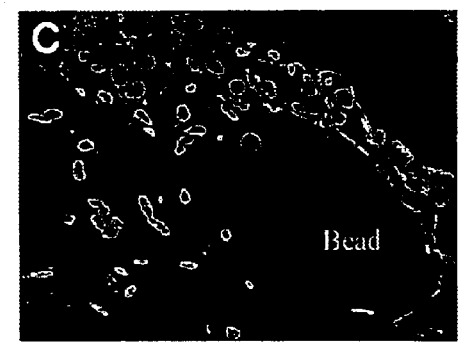

FIG. 2. Matrix deposition in Stage 1 roller bottle cultures. Panels A, B, and C show depositions of collagen types I, III, and IV, respectively. Collagen types I and III are deposited as broad bands surrounding the beads. Collagen type IV often formed basement membrane structures surrounding hepatocytes arranged in acinar or ductal configurations. Matrix is stained red whereas nuclei of the adjacent cells are stained blue. Visualization was by immunofluorescence microscopy.

Figure 3A:
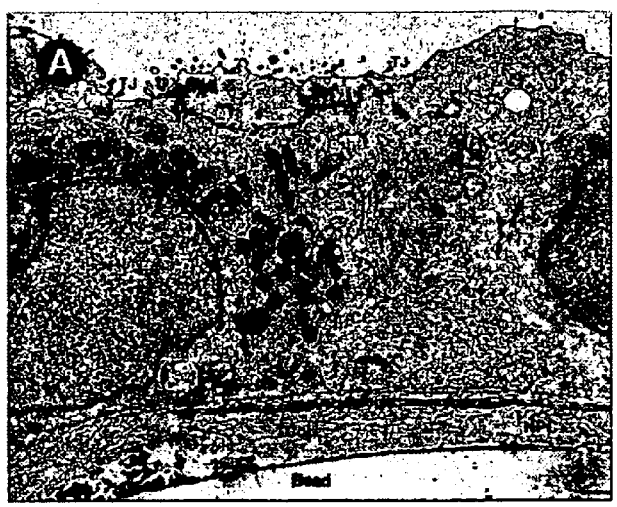
Figure 3B:
Figure 3C:

FIGS. 3A–C. Electron microscopy of cultures at Stage 1 (Roller bottle).

FIG. 3A. Low magnification view of hepatocytes growing on beads, before addition of Matrigel. Hepatocytes form a continuous multilayer or monolayer culture around the beads and display circuitous, interdigitated cell-cell contacts within the abluminal membrane. Canalicular structures (CC) and tight junctions (TJ) are seen. A 1-micron thick layer of fibrillar collagen (Col) is evident between the hepatocytes' abluminal membranes and the polystyrene bead. A nonparenchymal cell (NPC) is also seen within the fibrillar collagen layer. Bar=1 mmol/L.

FIG. 3B. Another view of the cytoplasmic features of hepatocytes at stage 1 (Magnification, 4,000×). Sinusoidal endothelial cells (SEC) are forming a layer of fenestrated endothelium. Fibrillar collagen (Col) and multiple microvilli are seen under the endothelial layer, with a morphology similar to that seen in the space of Disse.

Glycogen (Gly) and lamellae of rough endoplasmic reticulum (RER) are seen in the cytoplasm of the adjacent hepatocytes.

FIG. 3C. Higher magnification of B (10,000×) showing the fenestrae of the endothelial layer. Collagen fibrils are seen in the interrupted cytoplasmic continuity of the endothelial cell at the site of the formation of the fenestra.

Figure 4A:
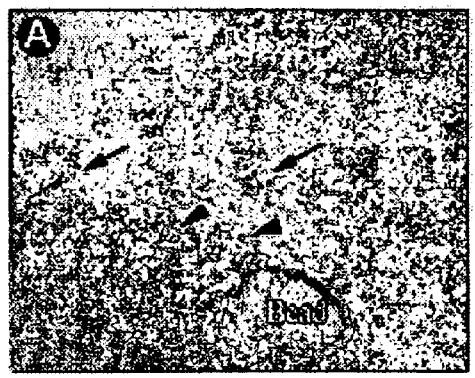
Figure 4B:
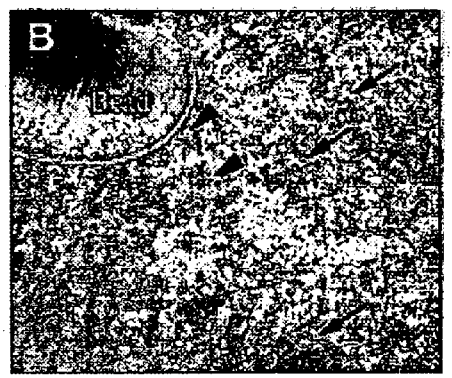
Figure 4C:
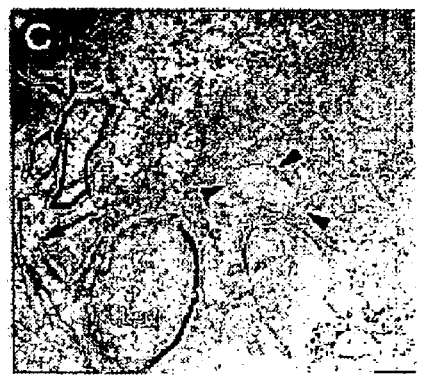

FIGS. 4A–C. Stains for macrophages, endothelial cells, and desmin-positive cells in Stage 1 roller bottle cultures. Visualization by differential interference microscopy. Positive immunohistochemistry is shown as red (complete arrows) whereas nuclei of cells are stained blue (truncated arrows).

FIG. 4A. Macrophages staining positive for ED-1 antigen. Note the "foamy" cytoplasm characteristic of macrophages in some of the cells.

FIG. 4B. Desmin-positive cells.

FIG. 4C. Structures of endothelial cells staining positive for 1CAM1 antigen. One of the endothelial cells contains a nucleus at the field of the image (complete arrow).

Figure 5A:
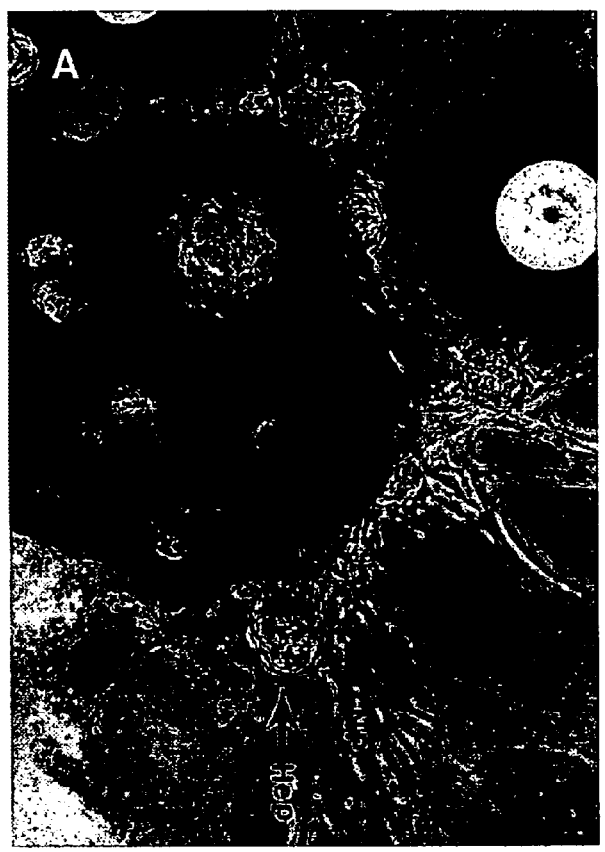
Figure 5B:

FIGS. 5A–B. Migration of cell populations from bead clusters after placement in Matrigel (Collaborative Biomedical, Mass.). Phase contrast microscopy.

FIG. 5A. Nonparenchymal cells (NP) migrate first and spread by attaching to the substratum. Occasional buddings of epithelial cells are seen at a higher focus plane (Hep). Some (arrow) appear to contain a duct. Culture at 1 week in Matrigel. Magnification, 200×.

FIG. 5B. Multiple buddings of epithelial cells migrate out of the bead clusters at different planes and in all directions. Culture at 20 days in Matrigel. Magnification, 200×.

Figure 6:

FIG. 6. Histology of the epithelial cell buddings in Matrigel at Stage 2 cultures at day 20 in Matrigel. Epithelial cells with hepatocyte morphology (see FIG. 8) are surrounding the central bead core and are arranged in sheets and ducts. Connective tissue deposition is also present underlying the epithelial cell structures. Hematoxylin eosin stain. Magnification, 200×.

Figure 7A:

FIG. 7A. Low power electron micrograph of an acinar structure formed from the bead cluster. Evident are the duct-like canalicular structures (C) in the center of the acinar structure. Cells contain extensive RER and numerous mitochondria. A thick, but less electron dense layer of extracellular matrix than that observed for the pre-Matrigel bead is seen between the hepatocytes and the bead, with several fibroblastic (F) type cells residing in the matrix. Bar–2 mm.

Figure 7B:
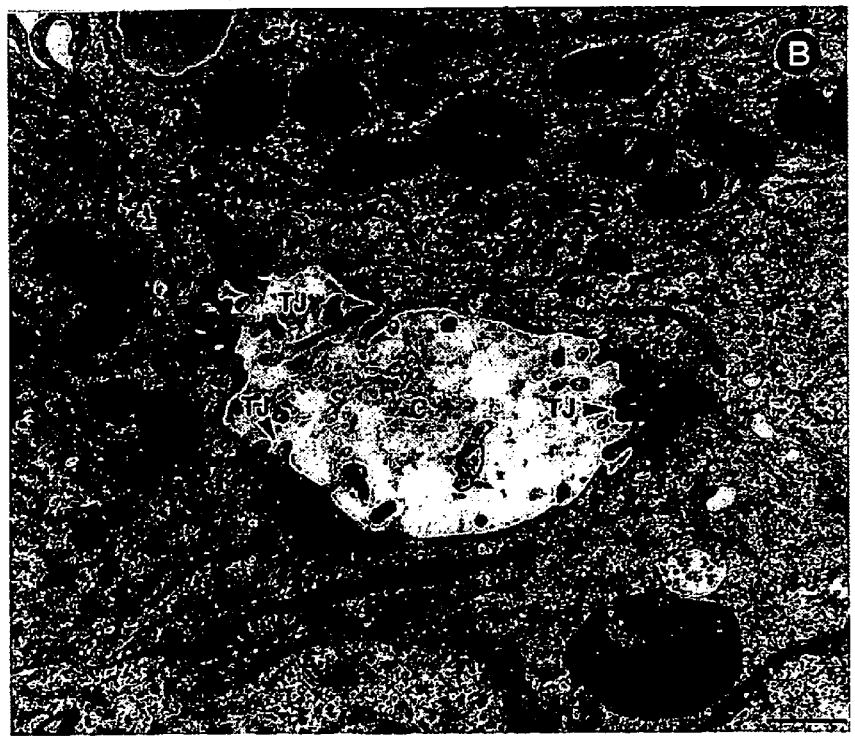

FIG. 7B. High power micrograph of the canalicular structure seen in A. Readily obvious are three extensive tight junctional areas (TJ), desmosomes, RER, Golgi elements, and Mt, mitochondria. Bar=500 nm.

Figure 8:
Figure 9A:
Figure 9B:
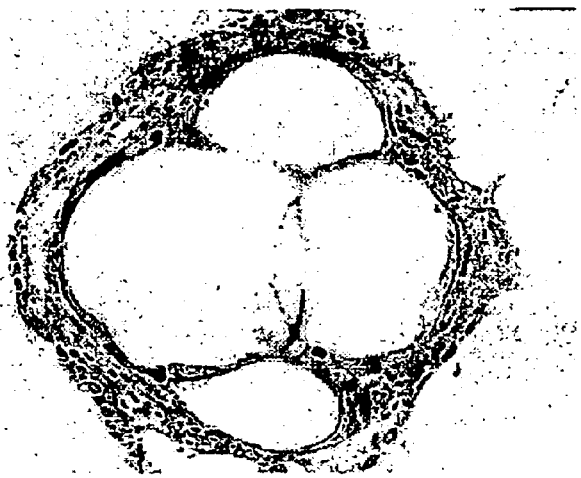
Figure 9C:
Figure 9D:

FIG. 8. Formation of plates by hepatocytes at Day 20 in Matrigel. Notice the prominent canalicular network (bright canals, arrows) along the middle of the plate.

FIG. 9. Cellular and matrix immunohistochemistry in Stage 2 cultures in Matrigel. Staining by immunoperoxidase. Panels A,B,C, and D show stains for desmin, Collagen types I, III, and IV, respectively. Desmin-positive stellate cells are interspersed in close proximity to the hepatocytes. Collagen type III shows the strongest immunohistochemical response. Collagen type IV often formed basement membrane structures surrounding hepatocytes arranged in acinar or ductal configurations (arrow).

Figure 10A:
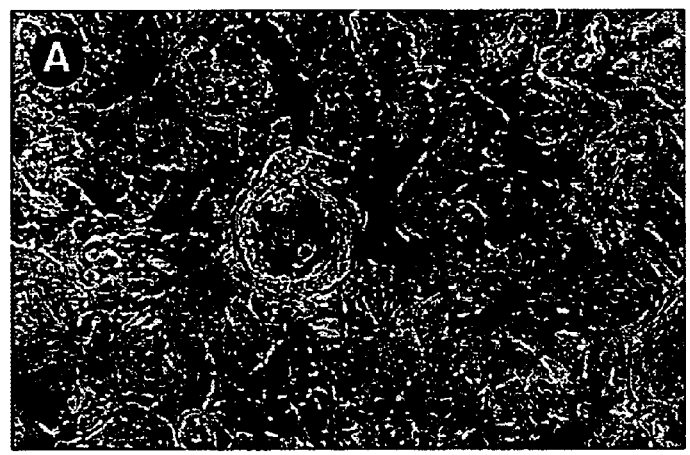

FIG. 10A Phase contrast microscopy of monolayers developing at 2 to 3 months in Matrigel (Stage 3 cultures) in the presence of HGF and EGF. Magnification 100×.

Figure 10B:
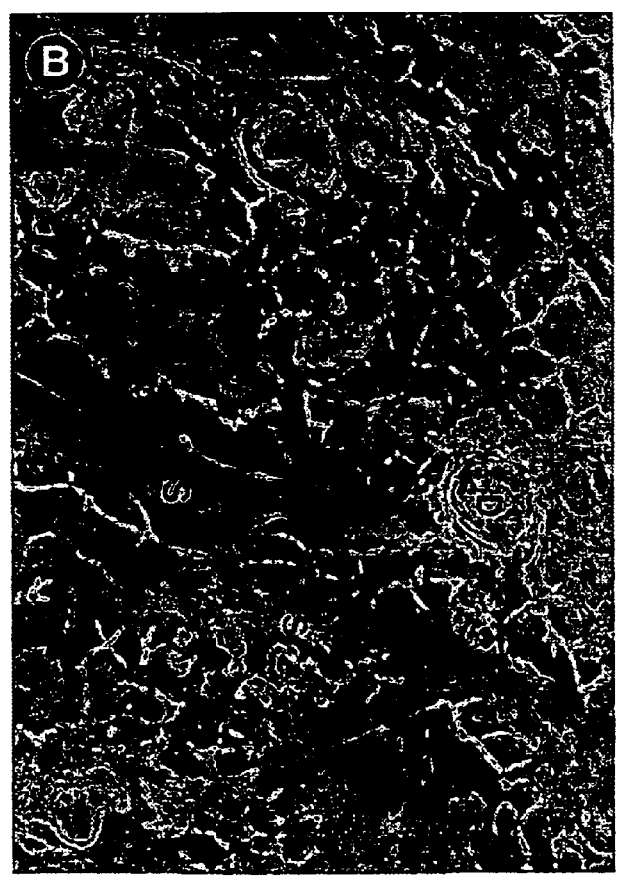

FIG. 10B. Magnification 200×. Notice the extensive canalicular network (bright lines ramifying with short branches along the hepatocyte plates), the pseudo-sinusoidal spaces (S), and the duct-like structures (D).

Figure 11A:
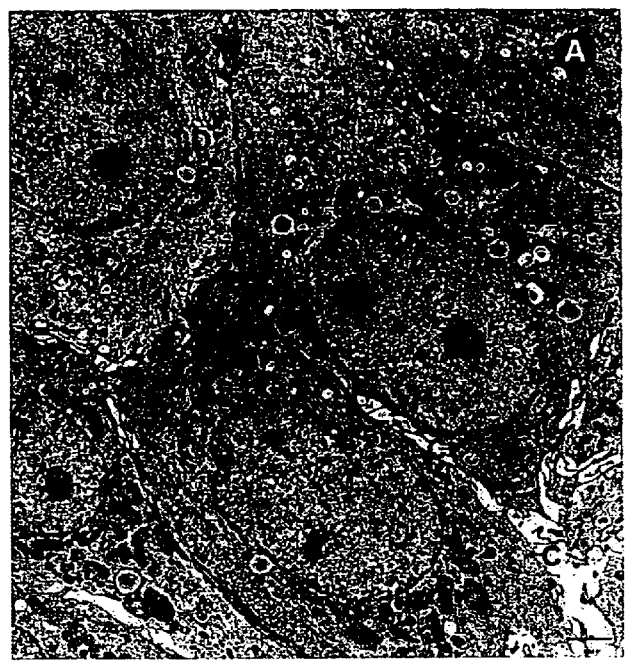

FIG. 11A. A low power (2,000×) electron micrograph of hepatocytes in Stage 3 cultures. Notice the longitudinal section of the extensive canalicular network (with microvilli and desmosomes) surrounding the individual hepatocytes.

Figure 11B:

FIG. 11B. Higher power view (10,000×) showing detailed cytoplasmic features. Rough endoplasmic reticulum, mitochondria, and Golgi network elements are seen in the individual hepatocytes.

Figure 12:

FIG. 12. Expression of several genes in hepatocytes immediately after isolation (Time zero), cells in roller bottle at day 13, cells in roller bottle at day 25, cells in Matrigel (Collaborative Research) cultures at day 25 (12 days after placement in Matrigel at Day 13), and nonparenchymal hepatic cell fraction (5% nonparenchymal hepatocyte contamination) immediately after isolation. Expression of GAPDH is used as a normalizing parameter.

Figure 13A:
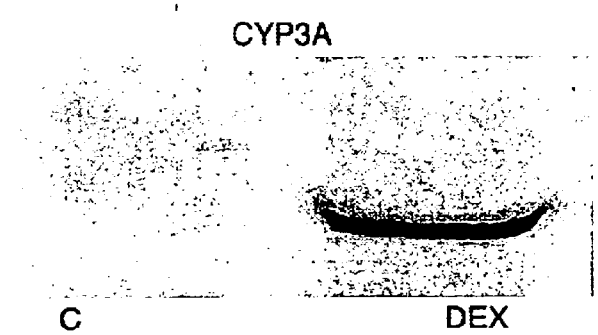
Figure 13B:
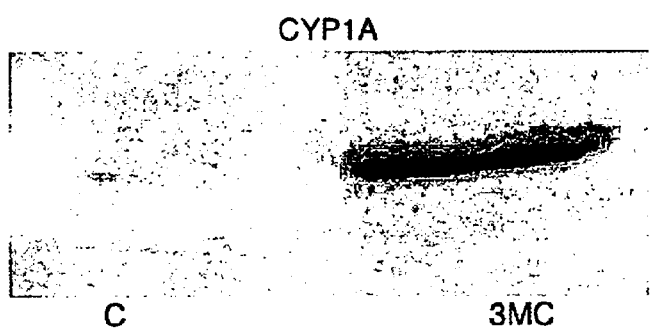
Figure 13C:

FIGS. 13A–C. Induction of the cytochrome P450 species CYP3A (FIG. 13A), CYP1A (FIG. 13B) and CYP2B1/2 (FIG. 13C) by their characteristic inducers in day 35 cultures. The increase in actual is demonstrated by western immunoblot. C stands for control. Dex (dexamethasone); 3MC (3' Methylcholanthrene); PB (Phenobarbital) were the inducers used correspondingly.

Figure 14:
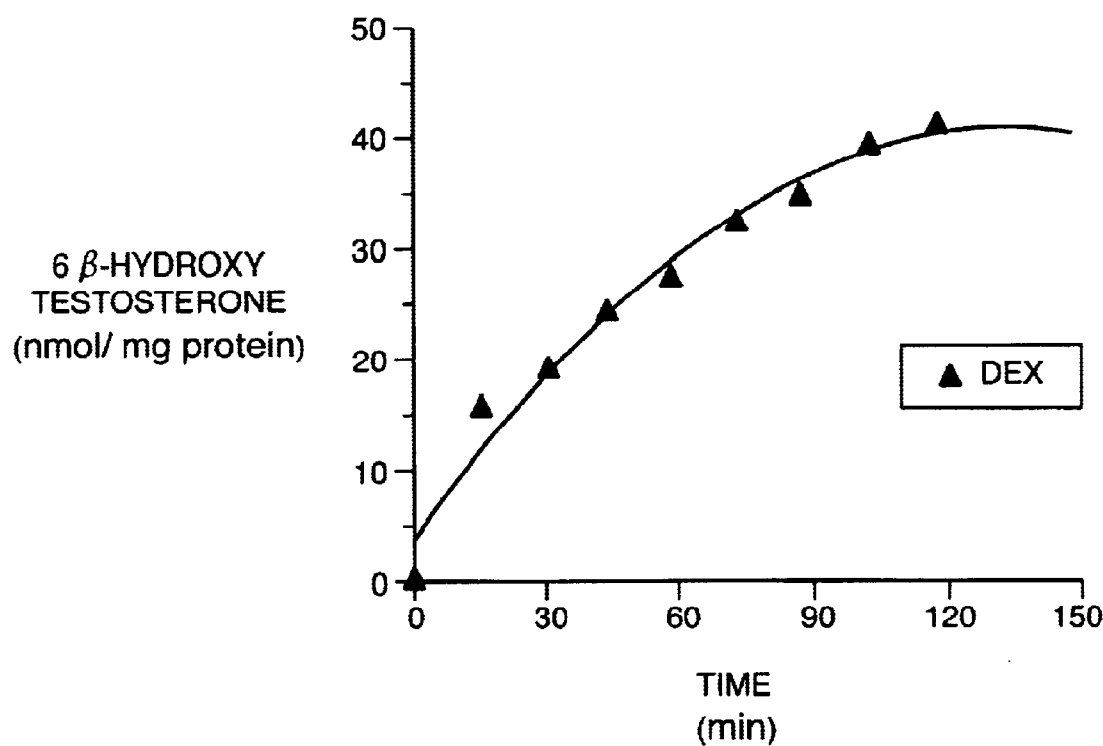
Figure 14:
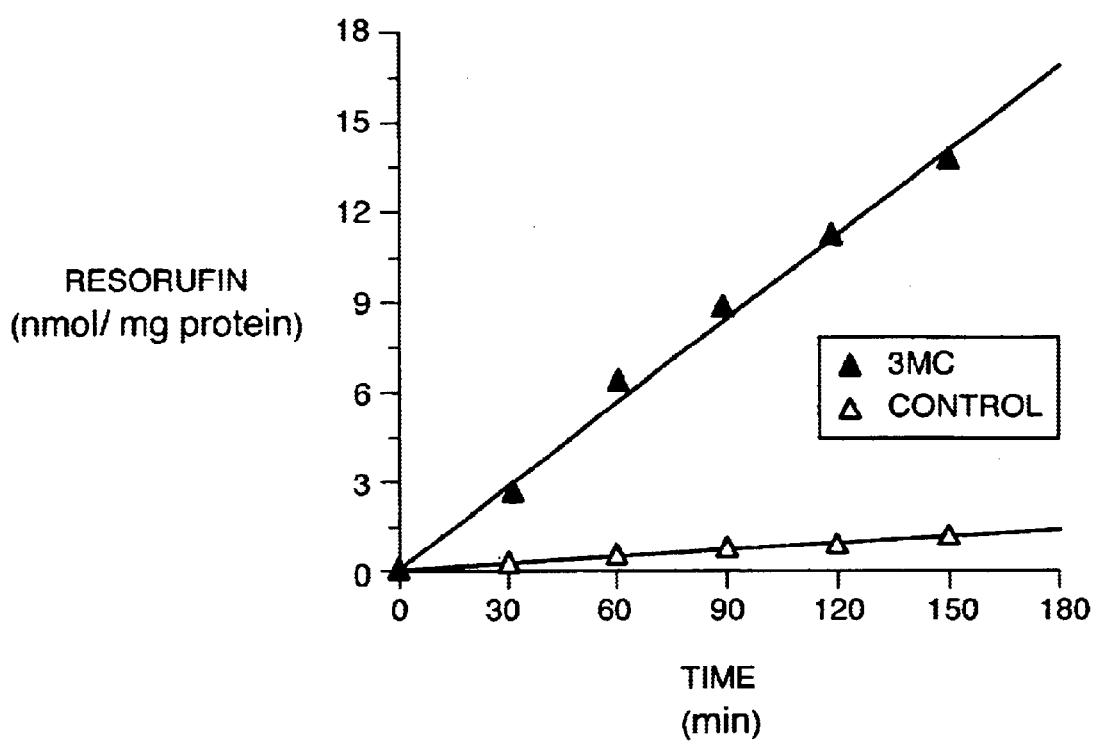

FIG. 14. Enzymatic Activities. The activities of testosterone 6β-hydroxylase (CYP3A dependent) and ethoxyresorufin O-deethylase (CYP1A dependent) were also measured in the same cultures. As demonstrated, more than 20-fold induction was seen in both cases by the characteristic inducers.

5. DETAILED DESCRIPTION OF THE INVENTION

The present invention relates to a novel tissue culture system that provides for long term culture of hepatocytes that retain their capacity to proliferate and express hepatic function. The invention provides compositions and methods for generating long term cultures of hepatocytes that can be used as bio-artificial livers for perfusion purposes. Alternatively, the hepatic cell culture systems may be implanted into a subject having a hepatic disorder to restore or supplement liver function.

The method of the present invention comprises the co-culturing of hepatocytes and nonparenchymal cells, in the presence of growth factors and a matrix material coated with at least one biologically active capable of a molecule promoting cell adhesion, proliferation or survival, thereby, resulting in the formation of matrix/hepatic cell clusters. The method of the present invention may further comprise the mixing of the matrix/hepatic cell clusters with a second matrix material that provides a three-dimensional structural support to form structures analogous to liver tissue found in vivo.

The compositions of the present invention include matrix/hepatic cell cultures comprising hepatocytes that retain their capacity to proliferate while expressing hepatic function. Further, the invention provides a three-dimensional hepatic cell culture system comprising hepatic cells that retain their capacity to proliferate and express hepatic function growing in a three-dimensional structure.

The hepatic cell system can be used for generating bio-artificial livers that function as perfusion devices for restoration of liver function. The three-dimensional matrix hepatic cell system can be administered to an individual for providing hepatic function in subjects with liver disorders. The matrix/hepatic cell system is administered in an effective amount necessary for restoration of liver function, thereby alleviating the symptoms associated with liver disorders.

5.1. Mixed Cultures of Hepatocytes and Nonparenchymal Cells

The present invention relates to methods for generating long term cultures of proliferating hepatocytes that retain their hepatic function. The method generally comprises co-culturing or propagating hepatocytes and nonparenchymal cells on a matrix coated with a biologically active molecule that promotes cell adhesion, in vitro. The cells are cultured under conditions effective and for a time sufficient to allow formation of a culture of proliferating hepatocytes that retain hepatic function. The cells are grown in the presence of growth factors that maintain hepatic cell differentiation and the capacity to proliferate.

Hepatocytes and nonparenchymal cells may be obtained from a variety of different donor sources. In a preferred embodiment, autologous cells are obtained from the subject who is to utilize the bio-artificial liver or receive the transplanted hepatic cells to avoid immunological rejection of foreign tissue. In yet another preferred embodiment of the invention, allogenic liver tissue for use in purifying cells may be obtained from donors who are genetically related to the recipient and share the same transplantation antigens on the surface of their hepatic cells. Alternatively, if a sibling is unavailable, tissue may be derived from antigenically matched (identified through a national registry) donors.

In an embodiment of the invention, hepatic cells and nonparenchymal cells are isolated from a disaggregated liver tissue biopsy. This may be readily accomplished using techniques known to those skilled in the art. For example, the liver tissue can be disaggregated mechanically and/or treated with digestive enzymes and/or chelating agents that weaken the connections between neighboring cells, making it possible to disperse the tissue suspension of individual cells. Enzymatic dissociation can be carried out by mincing the liver tissue and treating the minced tissue with any of a number of digestive enzymes. Such enzymes include, but are not limited to, trypsin, chymotrypsin, collagenase, elastase and/or hylauronidase. A review of tissue disaggregation techniques is provided in, e.g., Freshney, Culture of Animal Cells, A Manual of Basic Technique, 2d Ed., A. R. Liss, Inc., New York, 1987, Ch. 9, pp.107–126. In addition to primary cell cultures, established hepatic cell lines may also be utilized in the methods and compositions of the invention.

The present methods and compositions can also employ hepatic cells genetically engineered to enable them to produce a wide range of functionally active biologically active proteins, including but not limited to growth factors, cytokines, hormones, inhibitors of cytokines, peptide growth and differentiation factors. Additionally, the cells may be genetically engineered to increase their proliferative capacity, i.e, the cells may be immortalized. Methods which are well known to those skilled in the art can be used to construct expression vectors containing a nucleic acid encoding the protein coding region of interest operatively linked to appropriate transcriptional/translational control signals. See, for example, the techniques described in Sambrook, et al., 1992, Molecular Cloning, A Laboratory Manuel, Cold Spring Harbor Laboratory, N.Y., and Ausebel et al., 1989, Current Protocols in Molecular Biology, Greene Publishing Associates & Wiley Interscience, N.Y., incorporated herein by reference.

Once isolated, the hepatic and nonparenchymal cells can be grown in any culture medium known to those skilled in the art to support the growth and proliferation of such cells. For example, the mixed cultures of cells can be grown in chemically defined hepatocyte growth medium (HGM) supplemented with specific growth factors and regulatory factors. Such factors can be added to the culture media to enhance, alter or modulate proliferation and/or differentiation of the cultured hepatocytes and nonparenchymal cells. In a preferred embodiment of the invention, the culture media may be supplemented with growth factors such as hepatocyte growth factor (HGF) and/or epidermal growth factor (EGF), or functional homologs thereof, to impart phenotypic stability in terms of differentiated hepatocyte gene expression and the ability to proliferate.

In addition, the co-cultures of cells are propagated in the presence of a natural or synthetic matrix that provides support for hepatic cell growth during in vitro culturing. The type of matrix that may be used in the practice of the invention is virtually limitlessness. The matrix will have all the features commonly associated with being "biocompatible", in that it is in a form that does not produce an adverse, or allergic reaction when administered to the recipient host. In a preferred embodiment of the invention, the matrix is in the form of a bead to which the cultured cells may adhere. The beads may be composed of variety of different substances including, but not limited to, synthetic materials or naturally derived materials. The type of matrix material to be used will depend on the desired use of the hepatocyte cultures. For example, when the matrices are to be transplanted into a subject it is preferred that a biodegradable matrix material be used. For purposes of forming bio-artificial livers, the matrix may be composed of any suitable material to which the hepatocytes and nonparenchymal cells will adhere and proliferate.

Further, to improve hepatic cell adhesion, proliferation or survival, the matrix is coated on its external surface with factors known in the art to promote cell adhesion, growth or survival. Such factors include cell adhesion molecules, extra-cellular matrix molecules and/or growth factors for hepatocytes and/or nonparenchymal cells. Matrices may also be designed to allow for sustained release of growth factors over prolonged periods of time. Thus, appropriate matrices will ideally provide factors known to promote hepatic cell adhesion, growth or survival, and also act as a support on which the cultured cells differentiate and proliferate. In a preferred embodiment of the invention, the hepatic cell cultures are propagated in media containing matrices coated with collagen type I protein for promotion of cell adhesion and proliferation of bound hepatocytes.

The method of the present invention involves the co-culturing of hepatic and nonparenchymal cells in the presence of the selected matrix material. Although the cells may be propagated under static conditions, it is preferred that the cells arc propagated under mixing or stirring conditions wherein a cell suspension is combined with matrix, and mixed or stirred, to enhance the number and frequency of cell contacts with the matrix to maximize cell adhesion to the matrix, but not disrupt adherence to cells. Such conditions may be generated in variety of different ways including, for example, the use of roller bottles to provide continuous stirring or mixing of the culture. Preferably, the stirring is continued throughout the culturing of the hepatic and nonparenchymal cells.

The conditions of long-term matrix-cell culturing will preferably be maximized to enhance hepatocyte proliferation while maintaining hepatic function. Although certain variations in cell number, seeding techniques, culture media, incubation temperatures and incubation times, may be utilized, such variations would be routine to those skilled in the art and are encompassed by the present invention.

5.2. Preparation of Three-dimensional Culture Systems

The present invention further relates to the use of the matrix/hepatic/nonparenchymal cell clusters, produced as described in Section 5.1, for generation of three-dimensional hepatic cell culture systems to form structures analogous to liver tissue counterparts. The method of the invention comprises growing hepatic and nonparenchymal cells on a three-dimensional matrix in vitro under conditions effective and for a period of time sufficient to allow proliferation of the cells to form a three-dimensional structure.

The three-dimensional matrices to be used are structural matrices that provide a scaffold for the cells, to guide the process of tissue formation. Cells cultured on a three-dimensional matrix will grow in multiple layers to develop organotypic structures occurring in three dimensions such as ducts, plates, and spaces between plates that resemble sinusoidal areas, thereby forming new liver tissue. Thus, in preferred aspects, the present invention provides a three-dimensional, multi-layer cell and tissue culture system. The resulting liver tissue culture system survives for prolonged periods of time and performs liver-specific functions for use as a perfusion device or following transplantation into the recipient host.

A wide variety of structural matrices may be used in the context of the present invention for preparation of a three-dimensional hepatic cell culture system. In preferred embodiments, the matrices are bio-compatible matrices that provide a scaffold for the cells to guide the development of tissue. Preferred matrices are generally those that define a space for subsequent tissue development. Such matrices include hydrogels, biomatrix gels, or porous materials such as fiber based or sponge like matrices. The culture system described herein provides for the proliferation of cells to form structures analogous to liver tissue counterparts in vivo.

In certain embodiments, synthetic matrices, such as synthetic polymer matrices, may be used. Such matrices include, but are not limited to, nylon, dacron, polystyrene and homopolymers or heterpolymers such as polylactic acid (PLA) polymers, polyglycolic acid (PGA) polymers and polylactic acid-polyglycolic acid (PLGA) copolymer matrices. In other embodiments, matrices for use in the invention may be naturally-derived matrices extracted from or resembling extracellular matrix materials such as a collagen matrix, such as type I collagen. Other naturally derived matrix materials include laminin-rich gels, alginate, agarose and other polysaccharides, gelatin and hyaluronic acid derivatives. Certain matrix materials may not support efficient cellular attachment and, in such instances, it may be advantageous to coat the matrix with molecules that promote cell adhesion, such as extracellular matrix proteins or, specifically, collagen type I.

To generate the three-dimensional hepatic cell cultures, matrix/hepatic/nonparenchymal cell clusters generated as described above in Section 5.1 are isolated from cell culture suspensions. For example, the cell clusters may be isolated by low speed gravity sedimentation. The matrix/hepatic/nonparenchymal cell clusters are then exposed to a second structural matrix material in the presence of an appropriate culture media, thereby providing an environment for three-dimensional hepatic cell growth. Many commercially available culture media, supplemented in some instances with growth factors and the like, may be suitable for use. In addition, the culture media may be replenished periodically to provide a fresh supply of nutrients. The three-dimensional hepatic cell culture system is cultured for a sufficiently long period of time to allow the hepatic cells to replicate to form a three-dimensional cell or tissue structure.

Prior to use of three-dimensional hepatic cell cultures, the cultures may be contacted with a number of different growth factors that can regulate tissue regeneration by affecting cell proliferation, and gene expression. Such growth factors include those capable of stimulating the proliferation and/or differentiation of hepatic progenitor cells. For example, epidermal growth factor (EGF), transforming growth factor α (TGF-α) or hepatocyte growth factor (HGF) may be utilized. The hepatic cells may be stimulated in vitro prior to transplantation into the recipient subject, or alternatively, by injecting the recipient with growth factors following transplantation.

5.3. Use of the Hepatic Cell Cultures

The hepatic cell cultures of the invention can be used as bio-artificial livers for use by subjects having liver disorders that result in hepatic failure or insufficiency. The use of such bio-artificial livers involves the perfusion of the subject's blood through the bio-artificial liver. In the blood perfusion protocol, the subject's blood is withdrawn and passes into contact with the hepatocyte cell cultures. During such passage, molecules dissolved in the patient's blood, such as bilirubin, are taken up and metabolized by the hepatocyte cultures. In addition, the cultured hepatocytes provide factors normally supplied by liver tissue.

To form the bio-artificial liver the three-dimensional hepatocyte cell cultures of the invention are grown within a containment vessel containing an input and output outlet for passage of the subjects blood through the containment vessel. The bio-artificial liver further includes a blood input line which is operatively coupled to a conventional peristaltic pump. A blood output line is also included. Input and output lines are connected to appropriate arterial-venous fistulas which are implanted into, for example, the forearm of a subject. In addition, the containment vessel may contain input and output outlets for circulation of appropriate growth medium to the hepatocytes for continuous cell culture within the containment vessel.

In an embodiment of the invention, semipermeable membranes may be included in the bio-artificial livers to prevent direct contact of the subject's blood with the three-dimensional hepatocyte cultures. In such instances, the molecules dissolved in the subject's blood will diffuse through the semipermeable membrane and are taken up and metabolized by the hepatocyte cultures.

The use of the cultured hepatocyte systems of the invention to form bio-artificial livers provides a method which may be utilized to provide liver function to subjects suffering from hepatic failure or insufficiency.

The three-dimensional hepatic cell cultures can also be administered or transplanted to the recipient in an effective amount to achieve restoration of liver function, thereby alleviating the symptoms associated with liver disorders. When the hepatic cell cultures are to be administered to a recipient, it is desirable to form the hepatocyte cultures with hepatocytes and nonparenchymal cells derived from the recipient so as to avoid tissue rejection.

The number of cells needed to achieve the purposes of the present invention will vary depending on the degree of liver damage and the size, age and weight of the host. For example, the cells are administered in an amount effective to restore liver function. Determination of effective amounts is well within the capability of those skilled in the art. The effective dose may be determined by using a variety of different assays designed to detect restoration of liver function. The progress of the transplant recipient can be determined using assays that include blood tests known as liver function tests. Such liver function tests include assays for alkaline phosphatase, alanine transaminase, aspartate transaminase and bilirubin. In addition, recipients can be examined for presence or disappearance of features normally associated with liver disease such as, for example, jaundice, anemia, leukopenia, thrombocytopenia, increased heart rate, and high levels of insulin. Further, imaging tests such as ultrasound, computer assisted tomography (CAT) and magnetic resonance (MR) may be used to assay for liver function.

The three-dimensional hepatic cell system can be administered by conventional techniques such as injection of cells into the recipient host liver, injection into the portal vein, or surgical transplantation of cells into the recipient host liver. In some instances it may be necessary to administer the hepatic cell composition more than once to restore liver function. In addition, growth factors, such as G-CSF, or hormones, may be administered to the recipient prior to and following transplantation for the purpose of priming the recipients liver and blood to accept the transplanted cells and/or to generate an environment supportive of hepatic cell proliferation.

6. EXAMPLE

Mixed Cultures of Hepatocytes and Nonparenchymal Cells Maintained in Biological Matrices The purpose of the present example is the demonstration that mixed cultures of hepatocytes and nonparenchymal cells grown in chemically defined hepatocyte growth medium (HGM) containing hepatocyte growth factor and epidermal growth factor on collagen-coated polystyrene beads retain their hepatic functions while maintaining their capacity to proliferate.

6.1. Materials and Methods

6.1.1 Animals

Male Fischer 344 rats from Charles River were used for the studies described.

6.1.2 Reagents

EGF was obtained from Collaborative Biomedical (Waltham, Mass.).

Collagenase for hepatocyte isolation was obtained from Boehringer Mannheim (Mannheim, Germany). Vitrogen (Celtrix Labs., Palo Alto, Calif.) was used for the construction of the collagen gels. General reagents were obtained from Sigma (St. Louis, Mo.). EGF and Matrigel (Collaborative Research) were purchased from Collaborative Biomedical (Waltham,. Mass.). HGF used for these studies was the $\Delta 5$ variant and was kindly donated by Snow Brand. (Toshigi, Japan). Polystyrene beads coated with type I collagen were purchased from SoloHill Inc. (Ann Arbor, Mich.). Antibody sources: Mouse anti-rat ICAM (CD54) Pharmingen (San Diego, Calif.) (1:500); rabbit anti-rat collagen I, Chemicon (Temecula, Calif.) (1:100); rabbit anti-rat collagen III, Chemicon (1:100); Mouse anti-desmin, Dako (Carpenteria, Calif.) (1:100); Mouse anti-rat monocyte/macrophage (ED-1) Serotec (Raleigh, N.C.) (1:500); Rabbit anti-rat Collagen IV, gift from Dr. A. Martinez-Hernandez (1:100).

6.1.3 Isolation and Culture of Hepatocytes

Rat hepatocytes were isolated by an adaptation of Seglen's calcium two-step collagenase perfusion technique (Seglen, P. O., 1976, *Methods in Cell Biol.* 13:29–83) as previously described (Kost, D P et al., 1991, *J. Cell Physiol.* 147:274–289). Typically, a 3% contamination with non-parenchymal cells is seen in this isolate.

The nonparenchymal cell fraction was defined as the cell pellet isolated from the supernatant of the first low-gravity centrifugation used to prepare hepatocytes. This fraction primarily contains cells of Ito, bile duct cells, and endothelial cells. Small hepatocytes are also present in this fraction, typically comprising 5% of the cells.

6.1.4 Roller Bottle Cultures

Freshly isolated hepatocytes were added to roller bottles (850 cm$^2$ surface) obtained from Falcon (Franklin Lakes, N.J.). Each bottle contained $18.7 \times 10^6$ polystyrene beads and $210 \times 10^6$ freshly isolated hepatocytes in 250 mL of HGM medium supplemented with HGF (20 ng/mL) and EGF (10 ng/mL). The bottles were rotated at a rate of 2.5 rotations per minute and kept in an incubator maintained at 37° C., saturated humidity, and 5% $CO_2$. The viability of the cultures was assessed by periodic sampling. The samples were directly observed under a phase contrast microscope as well as stained with methyl tetrazolium to assess viability.

6.1.5 Cultures of Beads in Matrigel

The bead clusters containing cells were isolated from suspensions obtained from the roller bottle cultures. Enrichment for clusters was obtained by allowing for 2 minutes of unit gravity sedimentation. The bead and cell clusters were mixed with Matrigel (Collaborative Research). Bead clusters with attached cells were allowed to settle whereas beads without cells stayed mostly in suspension. The supernatant was aspirated leaving the, clusters in the bottom of the tube. The process was repeated three times. Clusters suspended in medium were mixed with Matrigel at a volume ratio of 1:4 (medium plus beads: Matrigel). Approximately 50 to 100 bead clusters were randomly embedded in Matrigel.

6.1.6 Composition of the HGM

HGM was prepared as previously described (Block, G. D. et al., 1996, *J. Cell Biology* 132:1133–1149). DMEM medium powder, HEPES, glutamine, and antibiotics were purchased from GIBCO/BRL (Grand Island, N.Y.). ITS mixture (Insulin, Transferrin, Selenium) was purchased from Boehringer Mannheim. All other additives were cell-culture grade (Sigma). Unless otherwise indicated for specific experiments, the basal HGM consisted of DMEM supplemented with purified bovine albumin (2.0 g/L), glucose (2.0 g/L), galactose (2.0 g/L), ornithine (0.1 g/L), proline (0.030 g/L), nicotinamide (0.305 g/L), $ZnCl_2$ (0.544 mg/L), $ZnSO_4$; $7H_2O$ (0.750 mg/L), $CuSO_4:5H_2O$ (0.20 mg/L), $MnSO_4$ (0.025 mg/L), glutamine (5.0 mmol/L), and dexamethasone ($10^{-7}$ mol/L). Penicillin and streptomycin were added to the basal HGM at 100 Mg:/L and 100 $\mu$g/L, respectively. The mixed basal HGM was sterilized by filtration through a 0.22-$\mu$m low-protein—binding filter system, stored at 4° C., and used within 4 weeks. ITS 1.0 g/L, (right hip-insulin 5.0 mg/L, human transferrin 5.0 mg/L [30% diferric iron saturated], selenium 5.0 $\mu$g/L) was added after filtration immediately before use. The growth factors, as required, were added to HGM fresh at the specified concentrations every time the medium was changed.

6.1.7 Transmission Electron Microscopy

Samples for transmission electron microscopy were washed once in PBS with 1 mmol/L $MgCl_2$, 0.5 mmol/L $CaCl_2$, then fixed overnight at 4° C. in 2.5% glutaraldehyde in PBS. Samples were washed three times with PBS then postfixed in 1% OsO4, 1% KFe(CN)$_6$ in PBS for 1 hour at room temperature. Samples were washed three times in PBS, then dehydrated through graded series (30%–100%) of ethanol. Following three changes of 100% ethanol, samples were infiltrated with several changes of Polybed 812 resin (Polysciences, Warrington, Pa.) at room temperature, a change overnight at 4° C., then a final change, in the case of cells grown on monolayers, where Beem capsules, filled with resin, were inserted on top of areas of interest. Resin was hardened overnight at 37° C., then for 2 additional days at 65° C. While the resin was still warm, Beem capsules were pulled from the dish and analyzed to ensure that the cells did not remain on the dish. In some cases monolayers were re-embedded to obtain cross sections. Thick sections (300 μm), obtained using a Reichert (Vienna, Austria) ultra-microtome fitted with a diamond knife, were heated onto glass slides, stained with 1% Toluidine Blue, and rinsed with water. Ultra thin sections (60 nm) were collected on Formvar-coated (Fullam, Schenectady, N.Y.) grids and stained with 2% uranyl acetate in 50% methanol for 10 minutes, then 1% lead citrate for 7 minutes. Sections were analyzed and photographed on a JEOL JEM 1210 transmission electron microscope at 80 kV.

6.1.8 Immunofluorescence Microscopy

Samples from roller-bottle cultures were fixed in 2% paraformaldehyde and 0.01% glutaraldehyde in PBS for 1 hour. Liver seeds were then stabilized by dipping them in 3% gelatin in PBS, then refixing them in the above fixative for an additional 15 minutes. Samples were incubated in 2.3 mol/L sucrose in PBS at 4° C. overnight. Samples were mounted on screw stubs and snap-frozen in liquid nitrogen. Five hundred nanometer-thick frozen sections were cut on a FCS Ultracut Microtome (Reichert) fitted with a cryokit. Sections were attached to glass slides by adsorbed Cell-Tak (Collaborative Biomedical). Sections were washed in 0.5% BSA, 0.15% glycine in PBS (PBG buffer) three times to remove sucrose, then blocked with 5% goat serum in PBG buffer for 30 minutes. Sections were then stained with various antibodies in PBG buffer for 1 hour at room temperature, washed three times in PBG buffer then stained with Cy3-conjugated (goat antirabbit or antimouse) secondary antibodies (Jackson Immunolabs, Bar Harbor, Me.) for 1 hour. Sections were washed three times with PBG buffer, then once in PBS. Nuclei were stained with 0.1 mg/mL Hoechst (bisBenzimide) for 30 seconds, washed twice with PBS, then mounted on slides with use of gelvatol (23 g polyvinyl alcohol 2000, 50 mL glycerol, 0.1% sodium azide to 100 mL PBS), and viewed on an Olympus Provis epifluorescence microscope (Olympus America, Melville, N.Y.) also equipped for differential interference microscopy.

6.1.9 Analysis of Gene Expression by Northern Blots

Total RNA was extracted by use of RNAzol B® (Biotecx, Houston, Tex.). RNA extraction from roller-bottle cultures was performed by washing bead-cell clusters in phosphate buffered saline and further digestion of the clusters by adding an equal volume of Trypsin-Ethylenediaminetetraacetic acid (GIBCO-BRL) to the bead-cell suspension. The mixture was shaken at 37° C. for 10 minutes. The bead-cell clusters were further washed in S+M buffer at 4° C. three times. The bead-cell pellet was mixed with three volumes of RNAzol and purified according to the manufacturer's guidelines.

RNA was extracted from Matrigel (Collaborative Research) -embedded beads by vortexing using 2.0 mL of RNAzol B® (Biotecx) per 1 mL of beads in Matrigel and purified per the manufacturer's guidelines. RNA concentration and purity were determined routine spectrophotometry. Size separation of 20 μg RNA per lane was completed on denaturing 1% agarose gels and transferred to nylon membranes (Amersham, Piscataway, N.J.) by the capillary method. After cross-linking under ultraviolet light, membranes were hybridized overnight with specific complementary DNAs (as indicated in FIG. 12) that had been labeled with [α-$^{32}$P]dCTP using Amersham random primer kit. Membranes were subsequently washed under high stringency conditions and exposed to R film (photographic film) (Kodak, N.Y.) for 1 to 3 days. Quantification of the RNA hybridization bands was performed by laser densitomer.

6.1.10 Sources of Complementary DNA Probes

EGF-R (rat) was obtained from Dr. Sheldon Earp, University North Carolina at Chapel Hill; acidic fibroblast growth factor receptor from American Type Culture Collection (catalog number 78222); acidic fibroblast growth factor receptor from American Type Culture Collection (catalog number 65796); urokinase plasminogen activator originated from Dr. Jay Degen, University of Cincinnati; cytochrome IIB1 from Dr. Steve Strom (University of Pittsburgh); complementary DNAs for albumin, α-fetoprotein were generated by Dr. Joe Locker (University of Pittsburgh).

6.2. Results

6.2.1 Morphogenetic Events in Cultures of Different Stages

Stage 1: Cultures of Hepatocytes on Beads in Roller Bottles. Collagen-coated polystyrene beads, were placed in roller bottles at a ratio of $18.7 \times 10^6$ beads to $210 \times 10^6$ freshly isolated hepatocytes. HGF and EGF were added as standard supplements in the HGM medium of the roller bottle cultures. Cells attached to the beads and, within 2 to 3 weeks, formed clusters of beads bound together with mesenchymal cells surrounded by layers of epithelial cells. The mesenchymal cells concentrate toward the center of the cluster and surround the individual beads (FIGS. 1A and 1B). They are associated with heavy deposition of type I and type III collagen immediately against the surface of the bead (FIG. 2). The collagen bundles surround the mesenchymal cells. Collagen type IV was seen as a thin rim forming a basement membrane surrounding only acinar structures of epithelial cells. The epithelial cells grow outside of the mesenchymal cells and symmetrically surround the beads or make eccentric projections. The epithelial cells have characteristics of small mature hepatocytes, as shown by electron microscopy. They contain multiple mitochondria and minimal rough endoplasmic reticulum (FIG. 3). Mature bile canaliculi containing microvilli as defined by junctional complexes were occasionally seen. Most often, they appeared as spaces surrounded by hepatocytes and containing microvilli. The junctional complexes were not as clearly defined as after placement in Matrigel (Collaborative Research). Those cells that are on the surface of the clusters have visible microvilli, whereas those toward the interior do not. The epithelial cells form multiple cell layers from the mesenchymal cell layer of the cluster to the surface. The cytoplasmic details of the epithelial cells in the clusters are shown in FIG. 3B and 3C. Multiple lamellae of rough endoplasmic reticulum and glycogen deposition is seen. Notable is the occasional information of fenestrated endothelium surrounding the hepatocytes. The proliferating cellular nuclear antigen (PCNA) labeling index of the epithelial cells exceeded 70% in all clusters. The BRdU labeling index of epithelial cells varied from 10% to 15% in different clusters. The number of nonparenchymal cells varied from one cluster to another. FIG. 4 shows desmin-positive mesenchymal cells, presumably derived from stellate cells contaminating the original hepatocyte preparation, interspersed between the epithelial cells. Approximately 15% to 20% of the cells at this stage seem to belong to this category. ICAM1-positive endothelial cells are also seen in FIG. 4, occasionally forming ICAM1-positive luminal structures. Overall, less than 2% of the cells at this stage stained positive for this antibody. Macrophages, identified as ED-1-positive cells, are seen only insporadic clusters, representing less than 0.1% of the total cell population.

Stage 2: Cultures in the First 3 Weeks After Implantation in Matrigel. Clusters of beads with the mixed cell populations were placed in Matrigel (Collaborative Research) as described in Materials and Methods. This resulted in a series of cell migrations. Mesenchymal cells with stellate shape migrated out of the beads first at about day 4 to 5 and in many instances formed a mat surrounding the beads (FIG. 5A). Protrusions with rounded contours, appearing as buds, were seen extending randomly in all directions from the bead clusters at about day 7 to 10. Some of them (approximately 30%) appeared to contain ducts. The typical appearance of these cultures is shown in FIG. 5B. Sections of these bud structures stained with hematoxylin and eosin are shown in FIG. 6. The buds consisted primarily of hepatocytes arranged in acinar structures or in sheets. Electron microscopy (FIG. 7) showed enhanced cytoplasmic differentiation of hepatocytes compared with cells in the roller bottle. Hepatocytes in the buds contained abundant lamellae of rough endoplasmic reticulum, glycogen, and canaliculi with complete junctional complexes. The latter features are not seen in the hepatocytes before implantation in Matrigel. In most cultures, several long plates, 1 to 2 hepatocytes in width and 10 to 20 hepatocytes in length (FIG. 8), were seen. These structures averaged about 20 to 30 per plate, with plates of different length extending from most clusters. The plates typically developed into areas of the substratum that were free of other cell types. There were no visible nonparenchymal cells underlying or surrounding these plates. A typically demarcated and fully developed canalicular network was seen along the entire length of the plates. Many of these single plates contained ducts at the end. IL6 (10 ng/mL) added to the cultures augmented the number of duct structures and caused formation of ducts along the plates or in the monolayer patches of hepatocytes. TGF-β1 (at 0.5 ng/mL) inhibited formation of all structures that developed from epithelial cells (buds, plates, and ducts) though migration of the nonparenchymal cells was not inhibited. The full spectrum of changes was seen in the presence of HGF plus EGF. Cultures maintained in HGF or EGF alone showed fewer and more limited changes per cluster compared with those with both growth factors. The extensive budding of the epithelial cells was associated with cell proliferation as judged by staining for PCNA. The numbers of labeled hepatocytes in the Matrigel ranged from 40% to 80% of epithelial cells per cluster, with considerable variation seen from one site to the next or among clusters. The BRdU labeling index, indicating active DNA synthesis, varied from 10% to 15% per cluster. Desmin-positive cells were seen interspersed and surrounding the hepatocytes. Type IV collagen was seen often as a thin rim surrounding acinar structures of hepatocytes. Slight staining was seen for type I and stronger staining for type III collagen (FIG. 9).

Stage 3: Long-Term Cultures in Matrigel. Long-term follow-up showed that HGF or EGF added separately was not sufficient to maintain prolonged viability of the epithelial cells. By 3 months, no epithelial cells were present in cultures maintained in HGF or EGF alone, or in control cultures without the addition of growth factors. In cultures maintained with combined HGF plus EGF, large monolayer patches of hepatocytes ranging from 2 to 10 mm in diameter were seen (FIG. 10). These structures appear at the rate of 2 to 4 patches per plate. These patches had a cytoarchitecture of striking similarity to sections of the liver acinus. Single or double hepatocyte plates were seen extending in a linear or convoluted manner. Complete canalicular networks developed throughout the entire length of each of the plates. The plates were separated by spaces that, though resembling the sinusoidal spaces seen in the liver lobules, did not contain any cells. Occasional ducts were also present in random locations along the plate structures. Electron microscopy (FIG. 11) showed typical hepatocyte morphology with most features typically present in hepatocytes, including glycogen, abundant rough endoplasmic reticulum, microbodies, and bile canaliculi with mature junctional complexes.

Gene Expression Changes in Cultures at Stages 1 and 2. The expression of several genes was examined in cultures at stages 1 and 2. Monolayers at stage 3 were not available in sufficient numbers for RNA preparation. FIG. 12 compares expression of several genes in hepatocytes and nonparenchymal cells immediately after isolation from liver, cells from roller bottle cultures at day 13, cells from roller bottle cultures at day 25, and cell-bead clusters at 12 days after implantation in Matrigel (Collaborative Research) (day 25 after cell isolation). The first and last lanes show expression of the same genes respectively in hepatocytes and the nonparenchymal cell fraction, immediately after isolation from the rat liver. (several hepatocyte associated genes are expressed in this fraction as a result of contamination by small hepatocytes). Through Matrigel-enhanced expression of α-fetoprotein, cultures in the roller bottles and in Matrigel maintained high expression of albumin. EGF-receptor expression decreased in culture, whereas HGF-receptor expression was maintained in roller bottles and in Matrigel, though Matrigel caused a decrease in c-met expression, CYPB1 expression decreased gradually in the roller bottle cultures but was restored after addition of Matrigel. TGF-β1 expression, derived from the nonparenchymal cells present in the mixed cultures, was pronounced in the roller bottle cultures at stage 1 but suppressed by Matrigel in stage 2 cultures. The same was true for urokinase plasminogen activator and its receptor urokinase plasminogen activator-R Expression of transferrin and α-1 antitrypsin was also enhanced at stage 2. A separate study was conducted to evaluate induction of cytochrome P450 species in stage 1 cultures. Induction of cytochrome P450 species CYP1A, CYP3A, CYP2B1/2 was seen in response to 3' Methylcholanthrene, Dexamethasone, and Phenobarbital, respectively.

FIGS. 13A–C demonstrates induction of the cytochrome P450 species CYP3A (FIG. 13A), CYP1A (FIG. 13 B) and CYP2B1/2 (FIG. 13C) by their characteristic inducers in day 35 cultures. The increase demonstrated by western immunoblot. Dexamethasone, methylcholanthrene) and phenobarbital were the inducers used correspondingly. The activities of testosterone 6β-hydroxylase (CYP3A dependent) and ethoxyresorufin O-deethylase (CYP1A dependent) were also measured in the same cultures. As demonstrated in FIG. 14, more than 20-fold induction was seen in both cases by the characteristic inducers.

The present invention is not to be limited in scope by the specific embodiments described herein which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the claims. Various publications are cited herein, the contents of which are hereby incorporated, by reference, in their entireties.

We claim:

1. A population of hepatocytes and nonparenchymal cells, derived using a method comprising:

co-culturing hepatocytes and nonparenchymal cells, derived from disaggregated liver tissue, in the presence of (a) one or more growth factors that support the growth of hepatocytes comprising epidermal growth factor or hepatocyte growth factor and (b) beads coated with extracellular matrix protein that promotes cell adhesion under conditions sufficient to allow for the proliferation of said hepatocytes while retaining hepatic faction of said hepatocytes.

2. A method for generating a hepatic cell culture comprising:

co-culturing hepatocytes and nonparenchymal cells derived from disaggregated liver tissue, in the presence of (a) one or more growth factors that support the growth of hepatocytes comprising epidermal growth factor or hepatocyte growth factor and (b) beads coated with extracellular matrix protein that promotes cell adhesion under conditions sufficient to allow for the proliferation of said hepatocytes while retaining hepatic function of said hepatocytes.

3. The method of claim 2 wherein the beads are polystyrene beads.

4. The method of claim 2 wherein the extracellular matrix protein is type I collagen.

5. The method of claim 2 wherein the growth factor is epidermal growth factor.

6. The method of claim 2 wherein the growth factor is hepatocyte growth factor.

* * * * *